United States Patent
Kouzarides

(10) Patent No.: US 6,747,005 B1
(45) Date of Patent: Jun. 8, 2004

(54) ASSAYS, METHODS AND MEANS FOR MODULATING NUCLEAR LOCALIZATION

(75) Inventor: Tony Kouzarides, Cambridge (GB)

(73) Assignee: Chroma Therapeutics Limited, London (GB)

( * ) Notice: Subject to any disclaimer, the term of this patent is extended or adjusted under 35 U.S.C. 154(b) by 0 days.

(21) Appl. No.: 09/744,469

(22) PCT Filed: Aug. 20, 1999

(86) PCT No.: PCT/GB99/02731

§ 371 (c)(1),
(2), (4) Date: Jan. 25, 2001

(87) PCT Pub. No.: WO00/11478

PCT Pub. Date: Mar. 2, 2000

(30) Foreign Application Priority Data

Aug. 21, 1998 (GB) .............................................. 9818356

(51) Int. Cl.[7] ........................ A61K 38/00; G01N 33/68; C12Q 1/48
(52) U.S. Cl. ............................. 514/12; 514/2; 530/350; 530/300; 536/23.1; 435/6; 435/69.1; 435/15; 435/7.1
(58) Field of Search ........................ 514/12, 2; 530/300, 530/350; 435/6, 7.1, 15, 69.1; 536/23.1

(56) References Cited

PUBLICATIONS

Görich D.: "Transport into and out of the nucleus" The Embo Journal, vol. 17, No. 10, 1998, pp. 2721–2727.
Chrivia J C et al.: "Phosphorylated CREB Specifically to the Nuclear Protein CBP" Nature, GB, MacMillan Journals Ltd. London, vol. 365, pp. 855–859 (1993).
Yang X–J et al.: "A P300/CBP–Associated Factor That Competes With the Adenoviral Oncoporotein E1A" Nature, GB, MacMillan Journals Ltd. London, vol. 382, No. 8589, pp. 319–324 (1996).
Ullman, K. S. et al.: "Nuclear export receptors form Importin to exportin" Cell, vol. 90, Sep. 1997, pp. 967–970.
Parthun, M. R.: "The major cytoplasmic histone acetyltransferase in Yeast: links to chromatin replication and histone metabolism" Cell, vol. 87, Oct. 1996, pp. 85–94.

Primary Examiner—Christopher S. F. Low
Assistant Examiner—Chih-Min Kam
(74) Attorney, Agent, or Firm—Nixon & Vanderhye PC

(57) ABSTRACT

CBP histone acetyltransferase acetylates Importin α, affecting ability of Importin α to translate into the nucleus and import a cargo protein. Assays identify substances which modulate interaction between CBP and Importin α and acetylation of Importin α by CBP. Substances identified in the assays are useful for treatment of disorders in which Imporin α plays a role.

6 Claims, No Drawings

SEQUENCE LISTING

```
<160> NUMBER OF SEQ ID NOS: 2

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
 1               5

<210> SEQ ID NO 2
<211> LENGTH: 16
<212> TYPE: PRT
<213> ORGANISM: Xenopus laevis

<400> SEQUENCE: 2

Lys Arg Pro Ala Ala Ile Lys Lys Ala Gly Gln Ala Lys Lys Lys Lys
 1               5                  10                  15
```

ASSAYS, METHODS AND MEANS FOR MODULATING NUCLEAR LOCALIZATION

This application is a 371 of PCT/GB99/02731, filed Aug. 20, 1999, which claims the priority of United Kingdom Application No. 9818356.9, filed Aug. 21, 1998.

The present invention relates to screening methods, peptides, mimetics, and methods of use based on the surprising discovery and characterisation of an interaction between known proteins, and thus numerous cellular processes of interest in therapeutic contexts. The proteins in question are CBP and Importin α, it further being shown herein that CBP acetylates Importin α at residues affecting nuclear localisation of Importin α.

Various enzymes have been identified which acetylate histones, so called histone acetyl-transferases or "HAT"s. There are four families known of enzymes with such activity. These are GCN5 and P/CAF (Brownell, et al (1996), *Cell*, 84: 843–831 and Yang, et al (1996), *Nature*, 382: 319–3241), CBP and p300 (Bannister and Kouzarides (1996), *Nature*, 384: 641–643 and Ogryzko, et al (1996), *Cell*, 87: 953–959), SRCl and ACTR (Chen, et al (1997), *Cell*, 90: 569–580 and Spencer, et al (1997), *Nature*, 389: 194–198) and TAF250 (Mizzen, et al (1996), *Cell*, 87: 1261–1270). The precise in vivo targets of these enzymes are largely unknown. In vitro experiments suggest that recombinant enzymes may have specificity for distinct lysines within the same histone. Precisely how acetylation of a particular histone increases transcription is not known.

Recently, evidence has been provided that some proteins other than histones are acetylated. The p53 transcription factor and the basal transcription factors TFIIE and TFIIF have been shown to be acetylated (Imhof, et al (1997), *Current Biology*, 7: 689–692). In the case of p53 it has been shown that acetylation increases the DNA binding capacity of the protein (Gu and Roeder (1997), *Cell*, 90: 595–606).

The present invention is based on the surprising discovery that CBP interacts with and acetylates a molecule which is not a transcription factor—Importin α—and moreover that the acetylated residues are important for Importin α function.

Experimental work on this is described below and leads to various aspects of the present invention in which there is provided for modulation of interaction between CBP and Importin α, particularly acetylation of Importin α by CBP.

Various aspects of the present invention provide for the use of CBP and Importin α in screening methods and assays for agents which modulate interaction between CBP and Importin α, particularly acetylation of Importin α by CBP, and agents which modulate the ability of Importin α to enter and/or exit the nucleus, and especially ability of Importin α to transport into the nucleus a cargo molecule.

Importin α is a shuttling NLS ("nuclear localisation signal") receptor which mediates the import into the nucleus of NLS-containing proteins. Exemplary NLS's include the SV40 T antigen NLS (PKKKRKV) (SEQ ID NO:1) and the bipartite nucleoplasmin NLS (KRPAAIKKAGQAKKKK) (SEQ ID NO:2). NLS-containing proteins bind Importin α in the cytoplasm and are imported into the nucleus.

Importin α is also known as Karyopherin α, Kap60, and Srp1. In the cytoplasm, Importin α binds the NLS-containing cargo protein and also Importin β. Importin β docks the heterotrimeric complex to the nuclear pores. At the nucleoplasmic side, the complex disassembles, the cargo is released and Importin α returns to the cytoplasm bound to its export factor, CAS, to start a new round for import (for reviews see Görlich, 1998 *EMBO J.* 17: 2721–2727; Ullmann et al., 1997, *Cell* 90: 967–970).

Identification of key residues in Importin α acetylated by CBP may also be used in the design of peptide and non-peptidyl agents which modulate, particularly inhibit, acetylation of Importin α (i.e. the transfer of an acetyl group from acetylcoenzyme A to the ε-amino group of a lysine residue in the protein) by CBP or other acetylase enzyme, as discussed further below.

Methods of obtaining agents able to modulate interaction between CBP and Importin α include methods wherein a suitable end-point is used to assess interaction in the presence and absence of a test substance. Assay systems may be used to determine CBP acetylase activity and/or CBP interaction with Importin α and/or acetylation of Importin α by one or more other acetylases. For acetylation assays, full-length Importin α, truncated portions of Importin α, or portions of Importin α fused to other proteins (e.g. GST), or a suitable variant or derivative of any of these may be used. Peptide acetylation assays may be developed using peptides that correspond to the acetylated regions of Importin α. The acetylation of any of the above may be assayed by any of a variety of procedures such as discussed below and may be adapted to high throughput screening approaches. Generally of most interest is modulation of the acetylation of Importin α by CBP or other acetylase. Detailed disclosure in this respect is included below. It is worth noting, however, that combinatorial library technology provides an efficient way of testing a potentially vast number of different substances for ability to modulate an interaction with and/or activity of a polypeptide. Such libraries and their use are known in the art, for all manner of natural products, small molecules and peptides, among others. The use of peptide libraries may be preferred in certain circumstances.

Given the results reported herein on which the present invention is based, activators and inhibitors of CBP-associated acetylase activity or other acetylase able to acetylate Importin α may be identified and appropriate agents may be obtained, designed and used for any of a variety of purposes.

Modulation of Importin α function may be used in principle to influence delivery to the nucleus of any NLS-containing protein. A very large number of nuclear proteins can enter the nucleus from the cytoplasm by means of recognition of the NLS by Importin α. Such proteins include factors involved in replication, DNA repair, recombination, apoptosis, cell proliferation and many other processes.

NLS-containing proteins whose import into the nucleus may be manipulated by modulation of Importin α acetylation in accordance with the present invention include transcription factors which are held in an inactive state in the cytoplasm and are only functional when translocated to the nucleus. Examples of such proteins include NF-KB, NFAT, SMAD, STAT and β-Catenin (See for example Clevers and Van de Wetering, December 1997, TIG 13(12): 485–489; Heldin et al., 1997, *Nature* 390: 465–470; Darnell, 1997, *Science* 277: 1630–1635; Ghosh et al., 1998, *Annu. Rev. Immunol.* 16: 225–60; Rao et al., 1997, *Annu. Rev. Immunol* 15: 707–47. By way of example, β-Catenin stimulates transcription of an oncogenic pathway when it is nuclear. Mutations found in β-Catenin stabilise the protein, increase its nuclear import and stimulate its transcriptional activation capacity.

Control of cellular proliferation is of course of interest for treatment of neoplasias, tumours, cancer, psoriasis, arteriosclerosis and other hyper-proliferative disorders. Other disorders that may be treated by modulation of nuclear import in accordance with the present invention include any in which a factor imported into the nucleus plays a role.

Thus, various methods and uses of modulators, which inhibit or potentiate interaction of CBP and Importin α, and modulators that affect acetylation of Importin α, are provided as further aspects of the present invention. The purpose of disruption, interference with or modulation of interaction between CBP and Importin α, particularly the acetylation of Importin α by CBP may be to modulate any activity mediated by virtue of such interaction, as discussed above and further below. Acetylation of Importin α by one or more other acetylases may be modulated for the same or similar purposes.

The full amino acid sequence of the CBP protein has been elucidated and is set out in Chrivia et al. (1993) *Nature* 365: 855–859. Residues 1098–1758 of CBP have been shown to include CBP histone acetyltransferase activity.

Reference to acetylation of Importin α generally applies herein unless context requires otherwise to any of the Importin α's, but particularly NPI/hSRP1, hSRP1α, Qip/Importin α3, hSRP1γ, Importin α4, Importin α6, Importin α7, and Importin α Rch1, particularly Importin α7 and Importin α Rch1, most particularly Importin α Rch1 (Cuomo et al., 1994, *PNAS USA* 91: 6156–6160; Cortes et al., 1994, *PNAS USA*, 91: 7633–7637; Nachury et al., 1998, *PNAS USA*, 95: 582–587; Köhler et al., 1997, FEBS Letters, 417: 104–108;)

Experimental evidence reported below indicates that the lysines in Importin α which are acetylated are within a region which contains the binding site for Importin β, specifically for Importin α Rch1 within residues 10 to 53 and more specifically within residues 10–23. An agent capable of modulating interaction between CBP and Importin α may be capable of blocking interaction between CBP and one or more of the acetylated lysine residues in the various Importin α's, for Importin α Rch1 Lys 18, Lys 20, Lys 22, especially Lys 22.

In addition to interacting at the site of acetylation of Importin α, CBP and Importin α may interact at one or more other sites within either or both proteins. Affecting interaction at such a site may have an effect on acetylation of Importin α by CBP. Various fragments and derivatives of the proteins, particularly of Importin α, may be used to analyse this, using techniques such as alanine scanning and deletion analysis. The present invention encompasses modulation of interaction between CBP and Importin α at any site, preferably resulting in modulation of Importin α acetylation.

Other agents according to the present invention useful in modulating acetylation of Importin α and therefore one or more of its functions, modulate the acetyltransferase activity of the acetylase. Such agents may specifically inhibit the ability of CBP to acetylate Importin α. Assays and screens for such agents are provided in accordance with the present invention, along with the agents themselves and their use in modulating Importin α acetylation and in modulating Importin α function.

Agents useful in accordance with the present invention may be identified by screening techniques which involve determining whether an agent under test inhibits or disrupts the interaction of CBP protein or a suitable fragment thereof (e.g. including amino acid residues of the acetylase domain, or a smaller fragment of any of these regions) of CBP, with Importin α or a fragment thereof, or a suitable analogue, fragment or variant thereof.

Suitable fragments of CBP or Importin α include those which include residues which interact with the counterpart protein. Smaller fragments, and analogues and variants of this fragment may similarly be employed, e.g. as identified using techniques such as deletion analysis or alanine scanning.

Thus, the present invention provides a peptide fragment of CBP which is able to interact with Importin α and/or inhibit interaction between CBP and Importin α, particularly acetylation of Importin α by CBP, and provides a peptide fragment of Importin α which is able to interact with CBP and/or inhibit interaction between Importin α and CBP, particularly acetylation of Importin α by CBP, such peptide fragments being obtainable by means of deletion analysis and/or alanine scanning of the relevant protein—making an appropriate mutation in sequence, bringing together a mutated fragment of one of the proteins with the other or a fragment thereof and determining interaction, preferably acetylation of Importin α or fragment thereof. In preferred embodiments, the peptide is short, as discussed below, and may be a minimal portion that is able to interact with the relevant counterpart protein and/or inhibit the relevant interaction. The invention further provides peptide fragments of Importin α which are able to inhibit acetylation of Importin α at the relevant residues.

Other proteins may bind Importin α at an acetylation site, and may bind or not depending on whether the site is acetylated or not. A protein other than CBP may bind at any one or more of the relevant lysines when they are acetylated, but not when not acetylated. A protein other than CBP may bind at any one or more of the relevant lysines when they are not acetylated, but not when acetylated. Such proteins may be identified using standard methodology to identify interacting proteins. For instance, non-acetylated Importin α fragments may be used in two-hybrid screens and chemically acetylated peptides may be screened against peptide and protein libraries. The invention further extends to the use of Importin α and peptide fragments thereof including one or more of the relevant lysines, acetylated or not acetylated, for obtaining a peptide or protein (other than CBP) which binds at an acetylation site, particular a peptide or protein which binds or not depending on whether the site is acetylated or not. Further aspects of the invention provide assay methods for such peptides and proteins based on determining binding to Importin α or a peptide fragment thereof, acetylated or not acetylated at one or more of the relevant lysines. The invention further extends to assays for substances able to modulate interaction of such peptides or proteins with the relevant acetylation site, and to methods of modulating such interaction, also modulating agents.

Similar techniques may be employed to identify and obtain acetylases other than CBP able to acetylate Importin α. Also, cellular extracts may be fractionated using column chromatography and fractions assayed for acetylase activity using Importin α as substrate. Fractions which contain Importin acetylase activity may be examined for the presence of CBP or other acetylase using antibodies in Western blots.

As disclosed herein, the Importin α residues susceptible to acetylation are located in the Importin β binding site. Accordingly, acetylation of Importin α may be modulated in accordance with the present invention so as to disrupt or promote interaction between Importin α and Importin β. Assays for useful substance in accordance with various aspects and embodiments of the present invention may involve determining interaction between Importin α and Importin β.

Peptides in accordance with the present invention tend to be short, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6, 5 or less in length. Peptides according to the present invention may be about 10–40 amino acids in length, about 5–10, about 10–15, about 10–20, about 10–30, about 20–30, or about 30–40 amino acids in length. Peptides which are Importin α fragments may include one or more of the relevant lysine residues noted above (e.g. for Importin α Rch1 Lys 18, Lys 20, Lys 22, especially Lys 22).

The present invention also encompasses peptides which are sequence variants or derivatives of a wild type CBP or Importin α sequence, but which retain ability to interact with Importin α or CBP (respectively, as the case may be) and/or ability to modulate interaction between CBP and Importin α, particularly acetylation of Importin α by CBP, and/or ability to modulate acetylation of Importin α by one or more other acetylases.

Instead of using a wild-type CBP or Importin α fragment, a peptide or polypeptide may include an amino acid sequence which differs by one or more amino acid residues from the wild-type amino acid sequence, by one or more of addition, insertion, deletion and substitution of one or more amino acids. Thus, variants, derivatives, alleles, mutants and homologues, e.g. from other organisms, are included.

Preferably, the amino acid sequence shares homology with a fragment of the relevant CBP or Importin α fragment sequence shown preferably at least about 30%, or 40%, or 50%, or 60%, or 70%, or 75%, or 80%, or 85%, 90% or 95% homology. Thus, a peptide fragment of CBP or Importin α may include 1, 2, 3, 4, 5, greater than 5, or greater than 10 amino acid alterations such as substitutions with respect to the wild-type sequence.

A derivative of a peptide for which the specific sequence is disclosed herein may be in certain embodiments the same length or shorter than the specific peptide. In other embodiments the peptide sequence or a variant thereof may be included in a larger peptide, as discussed above, which may or may not include an additional portion of CBP or Importin α. 1, 2, 3, 4 or 5 or more additional amino acids, adjacent to the relevant specific peptide fragment in CBP or Importin α, or heterologous thereto may be included at one end or both ends of the peptide.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or more preferably using the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405–410), FASTA (which uses the method of Pearson and Lipman (1988) *PNAS USA* 85: 2444–2448), or the Smith-Waterman algorithm (Smith and Waterman (1981) *J. Mol Biol.* 147: 195–197), generally employing default parameters. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Homology may be over the full-length of the relevant polypeptide or may more preferably be over a contiguous sequence of about 15, 20, 25, 30, 40, 50, 75, 100 or more amino acids, compared with the relevant wild-type amino acid sequence.

At the nucleic acid level sequence identity may be assessed by means of hybridization of molecules under stringent conditions. The present invention extends to nucleic acid that hybridizes with any one or more of the specific sequences disclosed herein under stringent conditions.

For example, hybridizations may be performed, according to the method of Sambrook et al. (below) using a hybridization solution comprising: 5×SSC (wherein 'SSC'= 0.15 M sodium chloride; 0.15 M sodium citrate; pH 7), 5× Denhardt's reagent, 0.5–1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): $T_m=81.5° C.+16.6Log [Na+]+0.41$ (% G+C)–0.63 (% formamide)–600/#bp in duplex.

As an illustration of the above formula, using [Na+]= [0.368] and 50–% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

It is well known in the art to increase stringency of hybridisation gradually until only a few positive clones remain. Other suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

As noted, variant peptide sequences and peptide and non-peptide analogues and mimetics may be employed, as discussed further below.

Various aspects of the present invention provide a substance, which may be a single molecule or a composition including two or more components, which includes a peptide fragment of CBP, particularly within the CBP acetylase domain, or Importin α, particularly within the acetylated region of Importin α, a peptide consisting essentially of such a sequence, a peptide including a variant, derivative or analogue sequence, or a non-peptide analogue or mimetic which has the ability to interact with CBP or Importin α and/or modulate, disrupt or interfere with interaction between CBP and Importin α.

Variants include peptides in which individual amino acids can be substituted by other amino acids which are closely related as is understood in the art and indicated above.

Non-peptide mimetics of peptides are discussed further below.

As noted, a peptide according to the present invention and for use in various aspects of the present invention may include or consist essentially of a fragment of CBP or Importin α respectively. Where one or more additional amino acids are included, such amino acids may be from CBP or Importin α or may be heterologous or foreign to CBP or Importin α. A peptide may also be included within a larger fusion protein, particularly where the peptide is fused to a non-CBP or non-Importin α (i.e. heterologous or foreign) sequence, such as a polypeptide or protein domain.

The invention also includes derivatives of the peptides, including the peptide linked to a coupling partner, e.g. an effector molecule, a label, a drug, a toxin and/or a carrier or transport molecule, and/or a targeting molecule such as an antibody or binding fragment thereof or other ligand. Techniques for coupling the peptides of the invention to both peptidyl and non-peptidyl coupling partners are well known in the art. In one embodiment, the carrier molecule is a 16 aa peptide sequence derived from the homeodomain of Antennapedia (e.g. as sold under the name "Penetratin"), which can be coupled to a peptide via a terminal Cys residue. The "Penetratin" molecule and its properties are described in WO91/18981.

Peptides may be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a peptidyl molecule according to the present invention (peptide or polypeptide) is to express nucleic acid encoding it, by use of nucleic acid in an expression system.

Accordingly the present invention also provides in various aspects nucleic acid encoding the polypeptides and peptides of the invention.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as encompassing the RNA equivalent, with U substituted for T, unless the context requires otherwise.

Nucleic acid sequences encoding a polypeptide or peptide in accordance with the present invention can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992), given the nucleic acid sequence and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding CBP or Importin α fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the CBP or Importin α sequences can be made, e.g. using site directed mutagenesis, to lead to the expression of modified CBP or Importin α peptide or to take account of codon preference in the host cells used to express the nucleic acid.

In order to obtain expression of the nucleic acid sequences, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of E. coli, yeast, and eukaryotic cells such as COS or CHO cells.

Thus, the present invention also encompasses a method of making a polypeptide or peptide (as disclosed), the method including expression from nucleic acid encoding the polypeptide or peptide (generally nucleic acid according to the invention). This may conveniently be achieved by growing a host cell in culture, containing such a vector, under appropriate conditions which cause or allow expression of the polypeptide. Polypeptides and peptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing heterologous nucleic acid as disclosed herein.

The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid encoding a peptidyl molecule according to the present invention may take place in vivo by way of gene therapy, to disrupt or interfere with interaction between CBP and Importin α or otherwise affect Importin α acetylation.

Thus, a host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) Also, the presence of a mutant, allele, derivative or variant sequence within cells of an organism, particularly when in place of a homologous endogenous sequence, may allow the organism to be used as a model in testing and/or studying substances which modulate activity of the encoded polypeptide in vitro or are otherwise indicated to be of therapeutic potential. Knock-out mice, for instance, may be used to test for radiosensitivity. Conveniently, however, at least preliminary assays for such substances may be carried out in vitro, that is within host cells or in cell-free systems. Where an effect of a test compound is established on cells in vitro, those cells or cells of the same or similar type may be grafted into an appropriate host animal for in vivo testing.

For instance, Importin α function or activity may be measured in an animal system such as a tumour model, e.g. involving a xenograft, relying on active Importin α.

Suitable screening methods are conventional in the art. They include techniques such as radioimmunosassay, scintillation proximetry assay and ELISA methods. Suitably either the CBP protein or fragment or Importin α or fragment, or an analogue, derivative, variant or functional mimetic thereof, is immobilised whereupon the other is applied in the presence of the agents under test. In a scintillation proximetry assay a biotinylated protein fragment may be bound to streptavidin coated scintillant—impregnated beads (produced by Amersham). Binding of radiolabelled peptide is then measured by determination of radioactivity induced scintillation as the radioactive peptide binds to the immobilized fragment. Agents which intercept this are thus inhibitors of the interaction. Further ways and means of screening for agents which modulate interaction between CBP and Importin α are discussed below.

In one general aspect, the present invention provides an assay method for an agent with ability to modulate, e.g. disrupt or interfere with interaction between CBP and Importin α, the method including:

(a) bringing into contact a first substance including a peptide fragment of CBP or a derivative, variant or analogue thereof as disclosed, a second substance including the relevant fragment of Importin α or a variant, derivative or analogue thereof, and a test compound under conditions in which, in the absence of the test compound being an inhibitor, the first and second substances interact; and (b) determining interaction between the first and second substances.

A test compound which disrupts, reduces, interferes with or wholly or partially abolishes interaction between said substances (e.g. including a CBP fragment and including a Importin α fragment), and which may modulate CBP and/or Importin α activity, may thus be identified.

Agents which increase or potentiate interaction between the two substances may be identified using conditions which, in the absence of a positively-testing agent, prevent the substances interacting. As noted, such agents may be used to potentiate Importin α function, particularly the ability to import a cargo protein.

Another general aspect of the present invention provides an assay method for a substance able to interact with the relevant region of CBP or Importin α as the case may be, the method including:

(a) bringing into contact a substance which includes a peptide fragment of CBP which interacts with Importin α, or which includes a peptide fragment of Importin α which interacts with CBP, or a variant, derivative or analogue of such peptide fragment, as disclosed, and a test compound; and (b) determining interaction between said substance and the test compound.

A test compound found to interact with the relevant portion of CBP is a candidate for having and may be tested for ability to modulate, e.g. disrupt or interfere with, CBP interaction with Importin α and/or ability to affect Importin α and/or CBP activity or other activity mediated by CBP or Importin α as discussed already above.

Similarly, a test compound found to interact with the relevant portion of Importin α is a candidate for having and may be tested for ability to modulate, e.g. disrupt or interfere with, Importin α interaction with CBP and/or ability to affect CBP and/or Importin α activity or other activity mediated by Importin α or CBP as discussed elsewhere herein.

Another general aspect of the present invention provides an assay method for a substance able to affect Importin α activity, the method including:

(a) bringing into contact Importin α and a test compound; and (b) determining Importin α activity (e.g. ability to translocate into the nucleus and/or ability to import a cargo protein, such as a GFP-NLS reporter).

Importin α activity may be determined in the presence and absence of CBP to allow for an effect of a test compound on activity to be attributed to an effect on interaction between Importin α and CBP, preferably acetylation of Importin α by CBP (discussed further below).

Assessment of nuclear localisation of Importin α may be facilitated by the use of labelled Importin α, e.g. fluorescein-labelled, and/or labelled cargo protein.

The digitonin-permeabilised mammalian cell system has been exploited in the identification of rate limiting factors for protein import (Adam et al., 1990, J. Cell. Biol. 111: 807–816), and may be employed in assay systems according to aspects and embodiments of the present invention, especially where Importin α activity is to be assayed. In this system the cytoplasmic cell content is depleted but the nucleus remains intact and competent for import processes driven by addition of recombinant factors and an energy regenerating system; see Görlich et al, 1998, EMBO J. 17: 2721–2727; Kutay et al., 1997, Cell 90: 1061–1071; and references cited therein.

The precise format of an assay of the invention may be varied by those of skill in the art using routine skill and knowledge. For example, interaction between substances may be studied in vitro by labelling one with a detectable label and bringing it into contact with the other which has been immobilised on a solid support. Suitable detectable labels, especially for peptidyl substances include $^{35}$S-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of an in vivo assay. The in vivo assay may be performed in a cell line such as a yeast strain or mammalian cell line in which the relevant polypeptides or peptides are expressed from one or more vectors introduced into the cell.

The yeast homologue of Importin α is known as SRP1 (Yano et al., (1992) Mol. Cel. Biol. 12: 5640–5651). It and/or one or more yeast acetylases such as GCN5 and ESA1 may be employed in assays in yeast, allowing for high-throughput screening.

The ability of a test compound to modulate interaction between CBP and Importin α may be determined using a so-called two-hybrid assay.

For example, a polypeptide or peptide containing a fragment of CBP or Importin α as the case may be, or a peptidyl analogue or variant thereof as disclosed, may be fused to a DNA binding domain such as that of the yeast transcription factor GAL 4. (A particularly preferred fragment of CBP may include or be the acetylase domain or a fragment of the acetylase domain.) The GAL 4 transcription factor includes two functional domains. These domains are the DNA binding domain (GAL4DBD) and the GAL4 transcriptional activation domain (GAL4TAD). By fusing one polypeptide or peptide to one of those domains and another polypeptide or peptide to the respective counterpart, a functional GAL 4 transcription factor is restored only when two polypeptides or peptides of interest interact. Thus, interaction of the polypeptides or peptides may be measured by the use of a reporter gene probably linked to a GAL 4 DNA binding site which is capable of activating transcription of said reporter gene. This assay format is described by Fields and Song, 1989, Nature 340; 245–246. This type of assay format can be used in both mammalian cells and in yeast. Other combinations of DNA binding domain and transcriptional activation domain are available in the art and may be preferred, such as the LexA DNA binding domain and the VP60 transcriptional activation domain.

When looking for peptides or other substances which interfere with interaction between a CBP polypeptide or peptide and Importin α polypeptide or peptide, the CBP or Importin α polypeptide or peptide may be employed as a fusion with (e.g.) the LexA DNA binding domain, and the counterpart Importin α or CBP polypeptide or peptide as a fusion with (e.g.) VP60, and involves a third expression cassette, which may be on a separate expression vector, from which a peptide or a library of peptides of diverse and/or random sequence may be expressed. A reduction in reporter gene expression (e.g. in the case of β-galactosidase a weakening of the blue colour) results from the presence of a peptide which disrupts the CBP/Importin α interaction, which interaction is required for transcriptional activation of the β-galactosidase gene. Where a test substance is not peptidyl and may not be expressed from encoding nucleic acid within a said third expression cassette, a similar system may be employed with the test substance supplied exogenously.

When performing a two-hybrid assay to look for substances which interfere with the interaction between two polypeptides or peptides it may be preferred to use mammalian cells instead of yeast cells. The same principles apply and appropriate methods are well known to those skilled in the art.

In preferred assays according to the present invention, the end-point of the assay, that is to say that which is determined in order to assess the effect of the test agent on the interaction of interest, is acetylation of Importin α or a fragment, variant or derivative thereof.

Thus, a further aspect of the present invention provides an assay method including:

(a) bringing into contact a substance which includes at least a fragment of CBP which acetylates Importin α, a substance which includes at least a fragment of Importin α including a site acetylated by CBP, and a test compound; and (b) determining acetylation at said site.

Of course, any suitable variant or derivative of CBP and/or Importin α may be employed in such an assay and any suitable fragments of Importin α may be employed including any of the sites of acetylation, such as including one or more of the relevant lysines as discussed above (e.g. for Importin α Rch1 Lys 18, Lys 20, Lys 22, especially Lys 22).

In determining the role of acetylated lysines in Importin α or homologue such as yeast SRP1, one or more lysines may be mutated to arginine (to eliminate acetylation) or to glutamine (to mimic acetylation). Such mutation analysis will be particularly useful in yeast systems, allowing for comparison of import of proteins such as a GFP-NLS reporter into the nucleus of wild-type and mutant hosts.

Another aspect of the present invention provides an assay method for a substance able to affect Importin α acetylation, the method including:

(a) treating acetylated Importin α with a test compound; and (b) determining acetylation of the Importin α.

A still further aspect of the present invention provides an assay method for a substance able to affect Importin α acetylation, the method including:

(a) treating with a test compound Importin α which is not acetylated at one or more of the relevant positions noted above; and (b) determining acetylation of the Importin α.

As noted, Importin α may be acetylated at one or more residues, particularly one or more of the lysine residues which correspond to Lys 18, Lys 20, Lys 22, especially Lys 22, in Importin α Rch1.

Acetylation may be determined for example by immobilising Importin α or a fragment, variant or derivative thereof, e.g. on a bead or plate, and detecting acetylation using an antibody or other binding molecule which binds the relevant site of acetylation with a different affinity when the site is acetylated from when the site is not acetylated. Such antibodies may be obtained by means of any standard technique as discussed elsewhere herein, e.g. using a acetylated peptide (such as a fragment of Importin α). Binding of a binding molecule which discriminates between the acetylated and non-acetylated form of Importin α or relevant fragment, variant or derivative thereof may be assessed using any technique available to those skilled in the art, which may involve determination of the presence of a suitable label.

As reported experimentally below, binding of antibody which recognises acetylated lysine is evidence that Importin α is acetylated in vivo. Chemically acetylated Importin α may be used to raise more specific and high affinity antibodies, as has been successfully achieved for acetylated histones. Such antibodies may be used to determine whether acetylation is primarily a nuclear or a cytoplasmic event.

Acetylation may also be assayed in solution, e.g. as described in Bannister and Kouzarides (1996), *Nature*, 384: 641–643. Briefly, protein substrate (~1 μg) and ~0.1 pmol of acetyltransferase are mixed to give a final volume of 30 μl in buffer IPH (50 mM Tris.HCl pH8.0, 150 mM NaCl, 5 mM EDTA, 0.5% [v/v] NP-40, 0.1 mM PMSF). Reactions are initiated by the addition of [14-C]-acetyl coA (1.85 kBq: 1.85 GBq/mmol; Amersham) and incubated at 30° C. for 10–45 min. The reaction products are then resolved by SDS-PAGE and viewed following fluorography of the gel. Alternatively, following SDS-PAGE, the resolved proteins can be Western blotted to a nitrocellulose membrane, which is then dried and exposed to film.

A further option is an in-gel activity assay, such as described by Brownell and Allis (1995), *Proc. Natl. Acad. Sci.*, 92: 6364–6368 or Mizzen, et al (1996), *Cell,* 87: 1261–1270. Samples may be crude cellular extracts, partially purified fractions, highly purified cellular proteins or bacterially produced and purified recombinant proteins. Before loading onto the activity gel the sample is made to 1×SDS-PAG loading buffer and boiled for 2 minutes. The gel is a standard Laemmli SDS-PAG except that purified protein substrate is added to the resolving gel to a final concentration of 1 mg/ml. Polymerisation of the gel is initiated using standard techniques, at which point the protein substrate becomes immobilized within the gel matrix. After adding the stacking gel, the samples are loaded and the gel run as a standard SDS-PAG. After the gel has run it is soaked, with gentle agitation, in 100 ml of wash buffer (50 mM Tris.HCl pH8.0, 0.1% β-mercaptoethanol) containing 20% (v/v) isopropanol for 20 minutes at room temperature. This washing step is repeated twice. Proteins in the gel are then denatured by washing in 100 ml of wash buffer containing 8M urea for 20 minutes at room temperature. This denaturing step is repeated twice. The gel is then soaked without agitation in 100 ml of wash buffer containing 0.04% tween-40 for 20 minutes at 4° C. This step is then repeated but for a duration of 12 hours, after which the gel is washed twice for a period of 20 minutes each time. After the final soak the gel/buffer is allowed to slowly come to room temperature. The gel is washed in wash buffer containing 10% (v/v) glycerol for 20 minutes at room temperature. The gel is then placed in a heat sealable bag and 3 ml of the same buffer containing 10 μCi of [3H]-acetylCoA is added. The contents are thoroughly mixed, air bubbles removed and the bag sealed. The reaction is then performed by immersing the bag in a 30° C. water-bath for at least 30 minutes. Following the acetylation step, the gel is recovered and washed extensively in several 100 ml changes of gel destain solution (10% [v/v] methanol, 10% [v/v] acetic acid). This washing stage is performed at room temperature with agitation and should include an overnight wash.

An agent able to inhibit acetylation of Importin α by CBP or other acetylase may include or other substance able to affect the catalytic properties of the enzymatically active site of the acetylase. An inhibitor of acetylation may interact with CBP or other acetylase within the acetylase domain. Residues within this domain are involved with interaction with Importin α and catalysis of the acetylation. Residues outside of the domain may also be involved in interacting with Importin α and agents which interfere with such interaction may affect the acetylation as discussed elsewhere herein.

Preliminary assays in vitro may be followed by, or run in parallel with, in vivo assays. of course, the person skilled in the art will design any appropriate control experiments with which to compare results obtained in test assays.

Performance of an assay method according to the present invention may be followed by isolation and/or manufacture and/or use of a compound, substance or molecule which tests positive for ability to modulate interaction between CBP and Importin α and/or modulate CBP or Importin α activity or a mediated activity. Following identification of a suitable agent it may be investigated further. Furthermore, it may be manufactured and/or used in preparation, i.e. manufacture or formulation, of a composition such as a medicament, pharmaceutical composition or drug. These may be administered to individuals.

The amount of test substance or compound which may be added to an assay of the invention will normally be determined by trial and error depending upon the type of compound used. Typically, from about 0.001 nM to 1 mM or more concentrations of putative inhibitor compound may be used, for example from 0.01 nM to 100 $\mu$M, e.g. 0.1 to 50 $\mu$M, such as about 10 $\mu$M. Greater concentrations may be used when a peptide is the test substance. Even a molecule which has a weak effect may be a useful lead compound for further investigation and development.

Compounds which may be used may be natural or synthetic chemical compounds used in drug screening programmes. Extracts of plants which contain several characterised or uncharacterised components may also be used.

Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction. The term "antibody molecule" may generally be used to cover antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

As noted above, antibody molecules may be used for determining whether or not a peptide or polypeptide (e.g. Importin α or fragment thereof) is acetylated, provided the relevant antibody molecule is able to discriminate between acetylated and non-acetylated forms of the peptide.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Antibodies may also be used in purifying and/or isolating a polypeptide or peptide according to the present invention, for instance following production of the polypeptide or peptide by expression from encoding nucleic acid therefor. Antibodies may be useful in a therapeutic context (which may include prophylaxis) to disrupt CBP and Importin α interaction with a view to inhibiting their activity. Antibodies can for instance be micro-injected into cells, e.g. at a tumour site, subject to radio- and/or chemo-therapy (as discussed already above). Antibodies may be employed in accordance with the present invention for other therapeutic and non-therapeutic purposes which are discussed elsewhere herein.

Other candidate inhibitor compounds may be based on modelling the 3-dimensional structure of a polypeptide or peptide fragment and using rational drug design to provide potential inhibitor compounds with particular molecular shape, size and charge characteristics.

A compound found to have the ability to affect CBP and/or Importin α activity has therapeutic and other potential in a number of contexts, as discussed. For therapeutic treatment such a compound may be used in combination with any other active substance, e.g. for anti-tumour therapy another anti-tumour compound or therapy, such as radiotherapy or chemotherapy. In such a case, the assay of the invention, when conducted in vivo, need not measure the degree of modulation of interaction between Importin α and CBP (or appropriate fragment, variant or derivative thereof) or of modulation of Importin α acetylation or activity caused by the compound being tested. Instead the effect on nuclear localisation may be determined. It may be that such a modified assay is run in parallel with or subsequent to the main assay of the invention in order to confirm that any such effect is as a result of the inhibition of interaction between CBP and Importin α caused by said inhibitor compound and not merely an unspecific effect or a general toxic effect.

Where a cargo protein of known effect on cellular function when localised in the nucleus is employed in an assay according to the invention, for instance a cargo protein which acts as a transcription factor, and/or has an effect on cellular proliferation, the effect caused or potentiated by nuclear localisation of the cargo may be determined. For instance, where the cargo is a transcription factor which promotes transcription from a particular promoter, expression from that promoter may be determined, e.g. by means of a suitable reporter gene construct. Similarly, where the cargo has an effect on cellular proliferation, the end-point of an assay according to the invention may cellular proliferation.

Thus, an agent identified using one or more primary screens (e.g. in a cell-free system) as having ability to interact with CBP and/or Importin α and/or modulate activity of CBP and/or Importin α may be assessed further using one or more secondary screens. A secondary screen may involve testing for a biological function of Importin α as noted above.

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the interaction between CBP and Importin α. Examples of such analogues include chemical compounds which are modelled to resemble the three dimensional structure of the CBP or Importin α domain in the contact area, and in particular the arrangement of the key amino acid residues as they appear in CBP or Importin α.

In a further aspect, the present invention provides the use of the above substances in methods of designing or screening for mimetics of the substances.

Accordingly, the present invention provides a method of designing mimetics of CBP or Importin α having the biological activity of Importin α or CBP binding or inhibition, the activity of allosteric inhibition of Importin α or CBP and/or the activity of modulating, e.g. inhibiting, CBP/Importin α interaction, said method including:
(i) analysing a substance having the biological activity to determine the amino acid residues essential and important for the activity to define a pharmacophore; and,
(ii) modelling the pharmacophore to design and/or screen candidate mimetics having the biological activity.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduced those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. some peptides may not be well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

The present invention further provides the use of a peptide which includes a sequence as disclosed, or a derivative, active portion, analogue, variant or mimetic, thereof able to interact with CBP or Importin α and/or modulate, inhibit or potentiate, interaction between CBP and Importin α and/or modulate, inhibit or potentiate, CBP and/or Importin α activity, in screening for a substance able to interact with Importin α and/or CBP, and/or modulate, inhibit or potentiate, interaction between CBP and Importin α, and/or modulate CEP and/or Importin α activity.

Generally, such a substance according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologicaly acceptable excipients. As noted below, a composition according to the present invention may include in addition to an modulator compound as disclosed, one or more other molecules of therapeutic use, such as an anti-tumour agent.

The present invention extends in various aspects not only to a substance identified as a modulator of CBP and Importin α interaction and/or CBP or Importin α-mediated activity, property or pathway, in accordance with what is disclosed herein, but also a pharmaceutical composition, medicament, drug or other composition including such a substance, a method including administration of such a composition to a patient, e.g. for a purpose discussed elsewhere herein, which may include preventative treatment, use of such a substance in manufacture of a composition for administration, e.g. for a purpose discussed elsewhere herein, and a method of making a pharmaceutical composition including admixing such a substance with a pharmaceutically acceptable excipient, vehicle or carrier, and optionally other ingredients.

A substance according to the present invention such as an inhibitor of CBP and Importin α interaction may be provided for use in a method of treatment of the human or animal body by therapy which affects an CBP or Importin α-mediated activity in cells, e.g. tumour cells. Other purposes of a method of treatment employing a substance in accordance with the present invention are discussed elsewhere herein.

Thus the invention further provides a method of modulating an CBP and/or Importin α-mediated activity, e.g. for a purpose discussed elsewhere herein, which includes administering an agent which modulates, inhibits or blocks the interaction of CBP with Importin α protein, such a method being useful in treatment where such modulation, inhibition or blocking is desirable, or an agent which increase, potentiates or strengthens interaction of CBP with Importin α, useful in treatment where this is desirable.

The invention further provides a method of treatment which includes administering to a patient an agent which interferes with the interaction of CBP with Importin α. Exemplary purposes of such treatment are discussed elsewhere herein.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated.

Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, e.g. in a viral vector (a variant of the VDEPT technique—see below). The vector may targeted to the specific cells to be treated, or it may contain regulatory elements which are switched on more or less selectively by the target cells.

The agent (e.g. small molecule, mimetic) may be administered in a precursor form, for conversion to the active form by an activating agent produced in, or targeted to, the cells to be treated. This type of approach is sometimes known as ADEPT or VDEPT, the former involving targeting the activator to the cells by conjugation to a cell-specific antibody, while the latter involves producing the activator, e.g. an enzyme, in a vector by expression from encoding DNA in a viral vector (see for example, EP-A-415731 and WO 90/07936).

An agent may be administered in a form which is inactive but which is converted to an active form in the body. For instance, the agent may be phosphorylated (e.g. to improve solubility) with the phosphate being cleaved to provide an active form of the agent in the body.

A composition may be administered alone or in combination with other treatments, either simultaneously or sequentially dependent upon the condition to be treated, such as cancer, virus infection or any other condition in which a CBP or Importin α-mediated effect is desirable.

Nucleic acid according to the present invention, encoding a polypeptide or peptide able to modulate, e.g. interfere with, CBP and Importin α interaction and/or induce or modulate activity or other CBP or Importin α-mediated cellular pathway or function, may be used in methods of gene therapy, for instance in treatment of individuals, e.g. with the aim of preventing or curing (wholly or partially) a disorder or for another purpose as discussed elsewhere herein.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A polypeptide, peptide or other substance able to modulate or interfere with the interaction of the relevant polypeptide, peptide or other substance as disclosed herein, or a nucleic acid molecule encoding a peptidyl such molecule, may be provided in a kit, e.g. sealed in a suitable container which protects its contents from the external environment. Such a kit may include instructions for use.

Various further aspects and embodiments of the present invention will be apparent to those skilled in the art in view of the present disclosure. Certain aspects and embodiments of the invention will now be illustrated by way of example.

EXPERIMENTAL

Recombinant Importin α Rch1 was shown to be acetylated by a recombinant CBP HAT domain (amino acids 1098–1758) at its N-terminus, i.e. within the first 95 residues. Approximately 1 µg of full-length Rch1, of a ΔN-Rch1 lacking the Importin β binding site, and of a N-terminal fragment (residues 1–95), were separately mixed with 0.1 pmol of the CBP acetyltransferase domain to give a final volume of 30 μl in buffer IPH (50 mM Tris.HCl pH8.0, 150 mM NaCl, 5 mM EDTA, 0.5% [v/v] NP-40, 0.1 mM PMSF). Reactions were initated by the addition of [14-C]-acetyl coA (1.85 kBq: 1.85 GBq/mmol; Amersham) and incubated at 30° C. for 30 min. The reaction products were then resolved by SDS-PAGE and Western blotted to a nitrocellulose membrane, which was dried and exposed to film. Only the full-length Rch1 and the N-terminal 1–95 fragment showed acetylation.

An antibody which recognises acetylated lysines was shown to recognise CBP-acetylated Importin α. Rch1 was incubated, either in the presence or absence of CBP, under conditions used in the experiment described above except that 50 μM non-radioactive acetyl coA replaced the $^{14}$C-labelled. After Western blotting, the blot was probed with a rabbit anti-acetylated-lysine antibody. After washing, the blot was probed with a secondary antibody (an anti-rabbit-antibody antibody) conjugated to horse radish peroxidase. After washing, the blot was developed using an ECL detection kit (Amersham). A band for Rch1 showing binding of the antibody was seen in the incubation in the presence of CBP, but not in the incubation in the absence of CBP.

In further experiments CBP was shown to acetylate Importin α family members, Rch1 and Importin α7, the analysis being performed as in the first experiment described above.

Acetylation site fine mapping was performed by deletion, localising the acetylated residues within residues 17 to 23, where there are three lysine residues (Lys18, Lys20 and Lys22). This region coincides with the region of Importin α which binds Importin β. Binding of Importin β is needed for nuclear import. Again, the various fragments of Importin α Rch1 were analysed as in the first experiment described above.

Acetylation of Importin α by CBP in vitro was shown to stimulate Importin α binding to Importin β. To parallel cultures of bacteria over-expressing His-tagged human Importin α were grown. $^{35}$S-methionine was added to one of the cultures. After four hours growth the His-tagged Importin α was purified from both cultures using Ni$^{2+}$ agarose beads, and the proteins was then eluted using standard techniques. The $^{35}$S-labelled Importin α was mock acetylated using conditions as in the experiments described above except no acetyl coA was added. The non-radioactive Importin α was acetylated exactly as described above. Equal amounts of the two human Importin α preparations were then incubated with z-tagged Importin β (bound to IgG-Sepharose) in binding buffer (50 mM Tris. HCl pH 7.5, 500 mM NaCl, 5 mM MgOAc, 10 mM β-mercaptoethanol). After extensive washing, the percentage (relative to input) of Importin α bound to Importin β was determined by PhosporImager analysis.

Further experiments showed that Lys 22 of Importin α is acetylated by CBP.

All documents mentioned anywhere herein are incorporated by reference.

What is claimed is:

1. An assay method for identifying an agent which affects one or more Importin α activities selected from the group consisting of (i) binding Importin β, (ii) translocating into the nucleus, and (iii) importing a cargo protein, the method comprising:
   (a) contacting Importin α and a test compound;
   (b) determining said one or more Importin α activities in the presence and absence of CBP (cAMP-response element binding protein) which acetylates Importin α, thereby determining the effect of CBP on said one or more activities; and
   (c) comparing said effect in the presence and absence of the test compound, wherein a difference in said effect in the presence relative to the absence of the test compound being indicative that said test compound is an agent which affects said one or more Importin α activities.

2. An assay method for identifying an inhibitory modulator of CBP (cAMP-response element binding protein) and Importin α binding, the method comprising:
   (a) contacting CBP, Importin α and a test compound;
   (b) determining the CBP and Importin α binding by comparison to CBP and Importin α binding in the absence of said test compound;

wherein inhibition of CBP and Importin α binding identifies said test compound as an inhibitory modulator of CBP and Importin α binding.

3. An assay method for identifying an agent which affects one or more activities of Importin α selected from the group consisting of (i) binding Importin β, (ii) translocating into the nucleus, and (iii) importing a cargo protein the method comprising:
   (a) contacting CBP (cAMP-response element binding protein) and a test compound;
   (b) determining CBP acetyltranferase activity in the presence and absence of a test compound;
   (c) comparing said CBP acetyltranferase activity in the presence and absence of test compound, wherein CBP acetylates Importin α and wherein a decrease in CBP acetyltransferase activity in the presence relative to the absence of the compound being indicative that the test compound is an agent which affects said one or more activities of Importin α; and
   (d) determining the effect of the test compound on one or more activities of Importin α selected from the group consisting of (i) binding Importin β, (ii) translocating into the nucleus and (iii) importing a cargo protein.

4. The method according to claim 3 comprising determining acetylation of Importin α by CBP.

5. An assay method for identifying an agent which binds to a region of CBP (cAMP-response element binding protein) or a region of Importin α, wherein the region of CBP binds to the region of Importin α, where acetylation of Importin α occurs, an agent which binds to said region of CBP or said region of Importin α being an inhibitory modulator of CBP and Importin α binding, the method comprising:
   (a) contacting CBP or Importin α and a test compound;
   (b) determining the binding between the CBP or Importin α and the test compound;
   (c) contacting CBP, Importin α and the test compound determined in step (b); and
   (d) determining the CBP and Importin α binding in the presence and absence of said test compound determined in step (b);
   wherein inhibition of CBP and Importin α binding identifies said test compound determined in step (b) as an inhibitory modulator of CBP and Importin α binding.

6. The method according to claim 1, claim 2, claim 3 or claim 5 further comprising formulating said agent into a composition comprising a pharmaceutically acceptable excipient.

* * * * *